United States Patent [19]

Lapidus

[11] Patent Number: 4,937,076

[45] Date of Patent: Jun. 26, 1990

[54] CHEWABLE ASPIRIN AND BUFFERING MATERIAL TABLET AND METHOD FOR PRODUCING SAME

[75] Inventor: Herbert Lapidus, Ridgefield, Conn.

[73] Assignee: Combe Incorporated, White Plains, N.Y.

[21] Appl. No.: 925,275

[22] Filed: Oct. 31, 1986

Related U.S. Application Data

[63] Continuation-in-part of Ser. No. 640,042, Aug. 10, 1984, abandoned.

[30] Foreign Application Priority Data

Dec. 13, 1984 [CA] Canada ................................... 470086

[51] Int. Cl.$^5$ ........................ A61K 31/60; A61K 9/26; A61K 9/50
[52] U.S. Cl. .................................... 424/441; 424/439; 514/165; 514/948; 514/951; 514/963
[58] Field of Search ................................. 424/439–441; 514/165, 948, 951, 963

[56] References Cited

U.S. PATENT DOCUMENTS

| | | | |
|---|---|---|---|
| 2,926,121 | 2/1961 | Hobbs et al. | 424/156 |
| 3,155,590 | 11/1964 | Miller et al. | 424/35 |
| 3,253,988 | 5/1966 | Scott | 424/156 |
| 3,341,416 | 9/1967 | Anderson et al. | 424/35 |
| 3,488,418 | 1/1970 | Holliday et al. | 424/35 |
| 3,524,910 | 8/1970 | Holliday et al. | 424/35 |
| 3,703,576 | 11/1972 | Kitajima et al. | 424/35 |
| 3,843,778 | 10/1974 | Diamond et al. | 424/38 |
| 4,163,777 | 8/1979 | Mitra | 424/157 |
| 4,199,560 | 4/1980 | Gyarmati et al. | 424/157 |
| 4,230,693 | 10/1980 | Izzo et al. | 424/156 |
| 4,303,648 | 12/1981 | Witzel et al. | 424/156 |
| 4,327,076 | 4/1982 | Puglia et al. | 424/38 |
| 4,327,077 | 4/1982 | Puglia et al. | 424/38 |
| 4,425,332 | 1/1984 | James | 424/157 |
| 4,533,543 | 8/1985 | Morris et al. | 424/38 |
| 4,710,384 | 12/1987 | Rotman | 424/470 |
| 4,749,575 | 1/1988 | Rotman | 424/441 |

FOREIGN PATENT DOCUMENTS

| | | | |
|---|---|---|---|
| 4921 | of 1877 | United Kingdom | 424/15 |
| 17875 | of 1909 | United Kingdom | 424/15 |
| 321965 | 11/1929 | United Kingdom | 424/15 |
| 1414121 | 11/1975 | United Kingdom | 424/157 |
| 2009597A | 6/1979 | United Kingdom | 424/156 |
| 2147501 | 5/1985 | United Kingdom . | |

OTHER PUBLICATIONS

New Gaines Dog Biscuits-Best News for Dogs Since Cats-General Foods Adv., Sunday Star Magazine, Washington, DC, Dec. 4, 1955.

Primary Examiner—Shep K. Rose
Attorney, Agent, or Firm—Roland T. Bryan

[57] ABSTRACT

A chewable aspirin and buffering material tablet and method for producing same is disclosed herein. In a single dosage form the aspirin and buffering materials are integrally dispersed and bound in a fatty material of chocolate, synthetic chocolate or hydrogenated tallow. The tablet is for gastrointestinal applications and is especially adopted for use with animals, particularly dogs, and can be molded into a variety of shapes including that of a miniature dog bone.

18 Claims, No Drawings

CHEWABLE ASPIRIN AND BUFFERING MATERIAL TABLET AND METHOD FOR PRODUCING SAME

This application is a continuation-in-part of my co-pending application, Ser. No. 06/640,042, filed Aug. 10, 1984 now abandoned.

BACKGROUND OF THE INVENTION

This invention relates to a chewable tablet containing aspirin in an integral and dispersed combination with a buffering material and the method for producing same. The tablets have use in those applications where aspirin is the prescribed treatment, but its associated undesirable and potentially harmful side effects are wanted to be avoided.

It has long been appreciated that the administration of aspirin with a buffering material has certain distinct advantages. One of these advantages is that the presence of a buffering material serves to increase the rate at which the aspirin is absorbed into the bloodstream. A second benefit is that the buffering material tends to decrease any irritation to the gastrointestinal mucosa that aspirin may cause in some subjects. This is especially true with animals such as dogs whose gastrointestinal tract is particularly sensitive to aspirin irritation.

Although the benefits of the coadministration of aspirin and a buffering material are recognized, the skill in the art for incorporation of these materials in a single dosage form has not developed a thoroughly acceptable product. The principal problem is that aspirin is known to be hydrolyzed to salicylic acid by the alkaline buffering material when moisture is present. This results in an aspirin product with reduced analgesic effectiveness.

U.S. Pat. No. 4,339,428, to Tencza, assigned to Bristol-Myers Co., describes the current level of skill in the art for an aspirin and alkaline tableted combination. Therein it is disclosed that aspirin and buffering material tablets have tried to be made stable by forming the tablets in two layers, one layer containing the aspirin and the other layer containing the buffering material. This has only proven to be relatively successful in providing a stable tablet i.e., one in which the aspirin is not readily hydrolyzed. However, even with the layering of the aspirin and buffering material, the effective aspirin content in a single table is reduced by the hydrolysis surrounding the aspirin alkaline interface.

In addition, such layering greatly increases the production costs of the tablets. Tablets are normally made by direct compression of the tableting products in the die chamber of a tablet press. With layered aspirin and buffer tablets, this requires a two-layered tablet press which is slower than a conventional single-layer machine and requires two separate and distinct compression steps, wherein each layer is separately formed and then joined.

In the administration of medication to animals, there is extreme difficulty in administering tablets and inducing swallowing, and also problems of controlling dosage; it is therefore desirable to have aspirin containing products in a fixed dosage, palatable and chewable form with an undetectable aspirin odor. While many pharmaceutical tablets are designed to be chewed to permit rapid activity in the digestive or circulatory system by increasing the available surface area for absorption of the drug, chewable aspirin buffering material combinations are known to cause an unpleasant oral reaction and leave an unpalatable taste due to chalkiness, grittiness, dryness, and astringent properties of these materials. These palatability and taste problems are also associated with such products administered in non-chewable tablet form, as the tablet tends to dissolve in the mouth before swallowing. Furthermore, in the production of chewable tablets, additional process steps and costs are necessarily encountered. In the production thereof, a disintegrating agent, such as alginic acid, can be added to the pre-tablet mix, and/or reduced compaction temperatures can be employed. However, these techniques cause undesirable mixture adhesion to the die chamber, and cause the tablets to be fragile and bitter.

U.S. Pat. No. 4,327,077, assigned to Life Savers, Inc., describes the current skill in the art to overcome taste and palatability problems. This is primarily accomplished by employing flavorings with the pharmaceuticals. While the flavorings do mask the unpleasant taste, they have not solved any of the associated palatability problems. To overcome palatability problems this same patent discloses a compressed chewable antacid tablet formed by binding the antacid in a fatty material. The fatty material and antacid are mixed and then recrystalized into a powder form and then compacted into a chewable tablet. This chewable tablet is disclosed as disintegrating quickly to a smooth, creamy, pleasant tasting emulsion devoid of grittiness. While the patent discloses a separate embodiment for aspirin and a fatty material, a combined aspirin buffering material tablet is not disclosed and the man skilled in the art would conclude it is not practicable since the disclosed recrystallization into powder form would only serve to integrate the aspirin and alkaline materials causing ultimate hydrolysis and reduction of aspirin into non-analgesic salicylic acid, which is sought to be avoided.

U.S. Pat. No. 4,339,428 discloses the current skill in the art for mixing aspirin and alkaline material in a capsule product wherein a high dosage of aspirin in powder or granulated form is mixed with an alkaline tablet. The capsules are produced by filling them first with the tableted alkaline material, and then adding thereto the aspirin composition in powder or granulated form. However, even with tableting the alkaline material separately from the aspirin, when the products are mixed in the capsule, hydrolysis problems of the aspirin are realized.

Thus, the prior art methods all teach that in a successful aspirin/buffering agent combination, steps must be taken to keep the aspirin and the buffering agent separate at all times until they have been ingested. If intimate contact of the two ingredients in the presence of moisture is allowed to occur to any significant degree, hydrolysis of the aspirin and a significant loss of its analgesic properties will result.

BRIEF SUMMARY OF THE INVENTION

It is accordingly an object of the present invention to provide a unique chewable tablet wherein aspirin and a buffering material are combined in a single dosage form. The aspirin/buffering materials are combined with a fatty material so that the aspirin and buffering materials are integrally dispersed and bound in said fatty material without significant reduction in the analgesic effectiveness of the aspirin.

It is a further object of the present invention to provide a method for making the above chewable tablet. This method includes the steps of melting the fatty material, separately admixing the aspirin and buffering materials with the melted fatty material batter, and then pouring said batter into the tablet molds for solidification and final tablet form.

Other and more detailed objects and features of this invention will be obvious from the following description and claims.

DETAILED DESCRIPTION OF THE INVENTION

In accordance with the present invention, a unique chewable aspirin and buffering material tablet is provided. The aspirin and buffering materials are combined with a fatty material so that the aspirin and buffering materials are individually coated and integrally dispersed and bound in said fatty material.

The principal ingredient on a weight basis of the chewable tablet will be the fatty material. The fatty material employed herein will preferably be in the form of chocolate or a synthetic chocolate such as "Ice-Cap" (a synthetic chocolate manufactured by Nestle, formed of hydrogenated fat, emulsifier, flavor, sugar, and milk solids).

This fatty material is preferred because the solid "Ice-Cap" provides excellent flavor, sweetness, aroma, and mouth feel. The "Ice-Cap" is also easy to handle and admix thereto and when melted is readily pourable having a comparable consistency to that of pancake batter. The "Ice-Cap" disclosed also assumes the shape of a mold without any sticking. Typically, the "Ice-Cap" is employed in an amount up to about 88% by weight of the finished chewable tablet.

Other fatty materials which may be employed herein in the amounts set out above are those which may be melted, mixed, and molded as described and exhibit the same excellent flavor, sweetness, aroma, and mouth feel characteristics. Examples of those materials suitable for use herein are natural chocolate and hydrogenated tallow. However, these materials are in no way to be taken as defining the whole class of suitable fatty materials limited for use herein.

To be added to the fatty material described hereinabove is aspirin (acetylsalicylic acid) which can be in the form of a powder or dry granulation that may vary widely in particle size. Preferably, a form of aspirin known in the art as "micronized aspirin" will be employed. See U.S. Pat. No. 4,339,428 for an example of usage. This is aspirin ground to a size of about 325-mesh aspirin. Another aspirin material suitable for use herein is known in the art as "microencapsulated" aspirin. Such a product may be obtained from Eurand America, Inc., of Dayton, Ohio. This is a micronized aspirin which has been encapsulated in a coating of ethyl-cellulose. Typically the aspirin content contained in a single dosage form will be 250 mg., or approximately 4 grains. However, this content can vary depending on tablet size, but the amount of aspirin in a tablet will be about 10% of the total tablet weight.

Also to be added to the fatty material is the buffering material or antacid. Examples of buffering materials or antacids suitable for use herein comprise any relatively water-soluble antacid acceptable to the Food & Drug Administration, such as aluminum carbonate, aluminum hydroxide (or as aluminum hydroxide-hexitol stabilized polymer, aluminum hydroxide-magnesium hydroxide codried gel, aluminum hydroxide-magnesium trisilicate codried gel, aluminum hydroxide-sucrose powder hydrated), aluminum phosphate, aluminum hydroxy carbonate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate, and or mixtures thereof.

Preferred buffering materials or antacids include aluminum hydroxide, calcium carbonate, magnesium carbonate and mixtures thereof, as well as magnesium hydroxide.

Typically the buffering material content contained in a single dosage form will be 50 mg. or approximately 1 grain. However, it is noted again that this content can vary depending on the tablet size, but the amount of antacid in a tablet will be about 2% of the total tablet weight.

While the aspirin, buffering, and fatty material constitute the principal ingredients of the invention, other ingredients may be added to the tablet to improve its physical or organoleptic characteristics or to facilitate the manufacture of the aspirin and buffering material tablet.

In carrying out the method of the present invention, each ingredient (aspirin and buffering material) will be dispersed within the fatty material separately. Surprisingly, this separate addition of the aspirin and the buffering material allows the two materials to be present together in the liquid system without interacting significantly. Without wishing to be bound by any theory, it appears that the first added component adsorbs a coating of molten fatty material which protects it from significant contact with the second component when it is added. In any case, for whatever reason, the separate addition of each component to the molten fatty material serves to prevent any significant reaction between them, not only during preparation, but thereafter as well. Thus the aspirin and the buffering material will be added to the fatty vehicle with continuous stirring until all the powdered material is completely dispersed and thereby coated. Thereafter, the dispersion can be poured onto Teflon-coated sheets and allowed to cool, until solidified, at which time the product sheets can be cut into any shape. Or, the dispersion may instead be fed into pre-formed molds where the dosage will solidify and remain discrete.

The following examples are given to further illustrate this invention. It is to be understood, however, that the invention is not limited thereto.

A chewable aspirin/buffering material tablet having the following composition is prepared as described below:

| Ingredient | Parts by Weight |
|---|---|
| "Ice-Cap" coating (Nestle) (fat, emulsifier, artificial flavor, sugar, milk solids) | 88.0 |
| Microencapsulated Aspirin EC #1 (Eurand America, Inc.) | 10.0 |
| Calcium Carbonate | 2.0 |

EXAMPLE 1

The following preparation is for approximately 7.65 kg. of the aspirin/buffering material product. The "Ice-Cap" coating (6.75 kg.) is melted in a jacketed mixing kettle at 120° F. The melt is then transferred to a Hobart-type mixer and under agitation, 0.75 kg. of the microencapsulated aspirin is added. Mixing is continued for several minutes until all the aspirin material is mixed into the "Ice-Cap." This mixture is then removed from the mixer, and 0.15 kg. of calcium carbonate is added. The mixture is mixed vigorously by hand, making sure that the calcium carbonate is uniformly distributed. The mixture is then poured onto Teflon-coated cookie sheets to a height of approximately ¼ inch. The mixture is covered, allowed to cool, and kept away from any source of moisture. When solidified, the mixture is cut into squares, each weighing 2.50 gm. Each square contains: 88% or 2.20 gm. of "Ice-Cap," 10% or 0.25 gm. of aspirin, and 2% or 0.050 gm. of calcium carbonate.

EXAMPLE 2

A preparation of 50 kg. of the buffered aspirin product is prepared as follows: To a stainless steel jacketed mixing kettle is added 44.0 kg. of "Ice-Cap" base. The "Ice-Cap" is heated slowly at a low mixer speed until it reaches 40°–50° C. When the "Ice-Cap" is molten, 5.0 kg. of microencapsulated aspirin (EC-1) is added, and mixing is continued at a medium mixer speed until the aspirin is completely dispersed. One (1) kilogram of calcium carbonate is then added, and the mixing continued until uniformly dispersed.

While the preceding method has disclosed spreading the batter mixture on Teflon-coated cookie sheets, it is also possible to practice the subject invention by pouring said batter into a mold and allowing the preparation to cool to 35° C. The solidifying product should be kept away from moisture, but may be allowed to cool in the air preferably at a relative humidity of 50% and at a temperature of 18°–21° C. When the preparation has cooled, it should be removed from the molds and immediately packaged in an airtight container.

In this case, the mold that was used was in the shape of a dog bone, and each molded tablet weighed 2.50 gm. comprised of the same percentage of components as described above.

The preparation from Example 1 was comparatively tested for shelf life and decomposition of aspirin to free salicylic acid against an unbuffered aspirin product. The testing was conducted using standard industry procedures for measuring free salicylic acid in aspirin products.

EXAMPLE 3

Hydrogenated fat (Durkee Paramount XX) (4.0 grams) was placed in a small beaker set in a water bath having a temperature slightly higher than the melting point (117°–119° F.) of the fat. When the fat was melted, micronized aspirin (Dow Chemical Co.) (0.250 grams) was added to the liquid fat and thoroughly dispersed by stirring with a glass rod. After all of the micronized aspirin was dispersed, finely divided calcium carbonate (0.05 gram) was added to the mixture and thoroughly dispersed by stirring with the glass rod. The mixture was removed from the water bath and was poured onto a Teflon-coated sheet to a height of approximately ⅛ inch. The mixture was covered and allowed to cool, and kept away from any source of moisture.

EXAMPLE 4

"Ice-Cap" (4.0 grams) was placed in a small beaker set in a water bath having a temperature slightly higher than the melting point of the fat. When the fat was melted, encapsulated aspirin EC #1 (0.250 grams) was added to the liquid fat and thoroughly dispersed by stirring with a glass rod. After all of the micronized aspirin was dispersed, finely divided aluminum hydroxide (0.05 gram) was added to the mixture and throughly dispersed by stirring with the glass rod. The mixture was removed from the water bath and was poured onto a Teflon-coated sheet of a height of approximately ⅛ inch. The mixture was covered and allowed to cool, and kept away from any source of moisture.

EXAMPLE 5

"Ice-Cap" (4.0 grams) was placed in a small beaker set in a water bath having a temperature slightly higher than the melting point of the fat. When the fat was melted, encapsulated aspirin EC #1 (0.250 grams) was added to the liquid fat and thoroughly dispersed by stirring with a glass rod. After all of the micronized aspirin was dispersed, finely divided magnesium oxide (0.05 gram) was added to the mixture and thoroughly dispersed by stirring with the glass rod. The mixture was removed from the water bath and was poured onto a Teflon-coated sheet to a height of approximately ⅛ inch. The mixture was covered and allowed to cool, and kept away from any source of moisture.

The preparation from Example 1 was comparatively tested for shelf life and decomposition of aspirin to free salicylic acid against an unbuffered aspirin product. The testing was conducted using standard industry procedures for measuring free salicylic acid in aspirin products.

The percent values tabled below were calculated as follows:

$$\text{mg. Free Salicylic Acid/gm. sample} = \frac{(\text{avg. peak area of the sample})}{(\text{av. peak area of the standard})} \times \frac{\text{amount of standard used } (100 \text{ mg.} \times 1/10)}{\text{sample weight (gm.)}} \quad (1)$$

$$\% \text{ Free Salicylic Acid} = \frac{\text{mg. Free Salicylic Acid/gm. sample}}{\text{mg. Total Salicylate/gm. sample}} \times 100\% \quad (2)$$

The results from the test:

| | | Unbuffered Aspirin/ "Ice-Cap" | | Buffered Aspirin/ "Ice-Cap" | |
|---|---|---|---|---|---|
| Time | Temp. | % Free Salicylic Acid | % Aspirin | % Free Salicylic Acid | % Aspirin |
| 1 month | 37° C. | 1.94 | 9.60 | 2.00 | 9.66 |
| 2 months | 37° C. | 3.33 | | 3.43 | |

The data presented shows no significant difference between the buffered and unbuffered products in the stability profile. This indicates that the dispersed buffering material is not accelerating the hydrolysis of the aspirin, and that the materials are separate. The unbuffered aspirin product is the same preparation as described in Example 1 with the exception that the calcium carbonate was omitted from the mixture.

Although the invention has been described with reference to specific forms thereof, it will be understood that many changes and modifications may be made without departing from the spirit of this invention.

I claim:

1. A chewable shelf-stable buffered aspirin tablet comprising:
   (a) a fatty material as a principal ingredient selected from a class consisting of chocolate, synthetic chocolate, and hydrogenated tallow,
   (b) as a minor ingredient by weight, unbuffered aspirin selected from a group consisting of granulated aspirin, micronized aspirin, powdered aspirin, microencapsulated aspirin, and mixtures thereof, and
   (c) as a minor ingredient, by weight, an amount of buffering material sufficient to buffer the effect of said aspirin on the gastrointestinal mucosa of a subject ingester, said buffering material being finely divided and selected from the class comprised of: aluminum carbonate, aluminum hydroxide (or as aluminum hydroxide-hexitol stabilized polymer, aluminum hydroxide-magnesium hydroxide codried gel, aluminum hydroxide-sucrose powder hydrated), aluminum phosphate, aluminum hydroxy carbonate, dihydroxyaluminum sodium carbonate, aluminum magnesium glycinate, dihydroxyaluminum aminoacetate, dihydroxyaluminum amionacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate, and mixtures thereof, said aspirin and buffering materials being individually separately coated by said fatty material whereby chemical reaction between the aspirin and buffering material is prevented, said aspirin and buffering material being uniformly dispersed and bound in said fatty material in a tablet form.

2. A chewable aspirin buffering tablet according to claim 1 wherein said fatty material contains up to about 40% by weight hydrogenated fats based on the weight of the tablet.

3. A chewable aspirin buffering tablet according to claim 1 wherein said finely divided buffering material is any relatively water-insoluble antacid.

4. A chewable aspirin buffering tablet according to claim 1 wherein said finely divided antacid is present in an amount not exceeding 2% by weight of said tablet.

5. A chewable aspirin buffering tablet according to claim 1 wherein said unbuffered aspirin is present in powder or granulated form of about 10% by weight of said tablet.

6. A chewable aspirin buffering tablet according to claim 5 wherein said unbuffered aspirin is microencapsulated in a porous but water-insoluble material.

7. A chewable aspirin buffering tablet according to claim 6 wherein said microencapsulating material is ethylcellulose.

8. A chewable aspirin buffering tablet according to claim 1 wherein said tablet is intended for use with animals.

9. A chewable aspirin buffering tablet according to claim 8 wherein said tablet is intended for use with dogs.

10. A chewable aspirin buffering tablet according to claim 9 wherein said tablet is molded in the shape of a dog bone.

11. A chewable aspirin buffering tablet comprising: a synthetic chocolate coating present in an amount of about 88% by weight of the tablet, ethyl-cellulose coated microencapsulated unbuffered aspirin present in an amount of about 10% by weight of the tablet, and a buffering material as finely divided calcium carbonate present in an amount of about 2% by weight of the tablet, said aspirin and buffering materials are separately coated by and integrally dispersed and bound in said fatty material whereby chemical reaction between the aspirin and the buffering material is prevented.

12. A chewable aspirin buffering tablet according to claim 11 wherein said tablet is intended for use with animals.

13. A chewable aspirin buffering tablet according to claim 12 wherein said tablet is intended for use with dogs.

14. A chewable aspirin buffering tablet according to claim 13 wherein said tablet is molded in the shape of a dog bone.

15. A method for producing the chewable tablet as defined in claim 1 which comprises melting the fatty material, admixing to said melt the aspirin, subsequently adding the buffering material to said mixture and stirring vigorously, pouring said mixture onto a sheet and cutting the solidified sheet into unit dosage forms.

16. A method for producing the chewable tablet as defined in claim 1 which comprises melting the fatty material, admixing to said melt the aspirin, subsequently adding the buffering material to said mixture and stirring vigorously, pouring said mixture into a mold and allowing the mixture to cool and solidify into single dosage form.

17. A method for producing the chewable tablet as defined in claim 16 wherein the mold is in the shape of a miniature dog bone.

18. A chewable aspirin buffering tablet according to claim 1 wherein said fatty material is present in an amount not exceeding about 88% by weight of said chewable tablet.

* * * * *